(12) United States Patent  
Piantoni et al.

(10) Patent No.: US 8,281,918 B2  
(45) Date of Patent: Oct. 9, 2012

(54) UNIT FOR TRANSFERRING PRODUCTS

(75) Inventors: Matteo Piantoni, Albino (IT); Alberto Perego, Milan (IT); Aldo Fusarpoli, Offanengo (IT)

(73) Assignee: GDM S.p.A. (IT)

( * ) Notice: Subject to any disclaimer, the term of this patent is extended or adjusted under 35 U.S.C. 154(b) by 225 days.

(21) Appl. No.: 12/808,624

(22) PCT Filed: Dec. 30, 2008

(86) PCT No.: PCT/IB2008/003647  
§ 371 (c)(1),  
(2), (4) Date: Jun. 16, 2010

(87) PCT Pub. No.: WO2009/083791  
PCT Pub. Date: Jul. 9, 2009

(65) Prior Publication Data  
US 2010/0270126 A1 Oct. 28, 2010

(30) Foreign Application Priority Data  
Jan. 3, 2008 (IT) ................ BO2008A0001

(51) Int. Cl.  
*B65G 47/84* (2006.01)  
*A61F 13/15* (2006.01)

(52) U.S. Cl. ............... 198/459.8; 198/471.1; 198/803.4; 198/803.5

(58) Field of Classification Search ............... 198/459.8, 198/471.1, 803.4, 803.5  
See application file for complete search history.

(56) References Cited

U.S. PATENT DOCUMENTS

| | | | |
|---|---|---|---|
| 4,596,545 A | 6/1986 | Greenwell | |
| 5,529,191 A | 6/1996 | Washeim | |
| 5,910,078 A | 6/1999 | Guttinger et al. | |
| 6,273,242 B1 | 8/2001 | Olson et al. | |
| 6,319,347 B1* | 11/2001 | Rajala et al. | 156/164 |
| 6,705,453 B2* | 3/2004 | Blumenthal et al. | 198/471.1 |
| 6,811,019 B2* | 11/2004 | Christian et al. | 198/471.1 |
| 6,814,217 B2* | 11/2004 | Blumenthal et al. | 198/459.8 |
| 7,165,668 B2* | 1/2007 | Dombek | 198/459.8 |
| 7,650,984 B2* | 1/2010 | Giuliani et al. | 198/471.1 |
| 2003/0066609 A1* | 4/2003 | Calvert | 156/362 |
| 2005/0281646 A1 | 12/2005 | Knuppel et al. | |

FOREIGN PATENT DOCUMENTS

| | | |
|---|---|---|
| EP | 0304044 | 2/1989 |
| EP | 0645308 | 3/1995 |
| EP | 1308147 | 5/2003 |
| EP | 1428487 | 6/2004 |
| EP | 1595828 | 11/2005 |
| WO | 9519752 | 7/1995 |
| WO | 9609962 | 4/1996 |
| WO | 03031177 | 4/2003 |

OTHER PUBLICATIONS

International Search Report and Written Opinion dated Mar. 27, 2009.

* cited by examiner

*Primary Examiner* — Mark A Deuble  
(74) *Attorney, Agent, or Firm* — Timothy J. Klima; Shuttleworth & Ingersoll, PLC

(57) ABSTRACT

Products are transferred in an automatic manufacturing machine by a unit (1) equipped with multiple transport heads (8), and a drive system (10) comprising at least two transmission assemblies (11a, 11b) by which the heads (8) are set in motion. The transport heads (8) are divided operationally into a first group (12) and a second group (13), in which motion is induced by a respective first transmission assembly (11a) and a respective second transmission assembly (11b).

17 Claims, 4 Drawing Sheets

UNIT FOR TRANSFERRING PRODUCTS

CROSS-REFERENCE TO RELATED APPLICATIONS

This application is the National Phase of International Application PCT/IB2008/003647 filed Dec. 30, 2008 which designated the U.S. and that International Application was published under PCT Article 21(2) in English.

This application claims priority to Italian Patent Application No. BO2008A000001 filed Jan. 3, 2008, and PCT Application No. PCT/IB2008/003647 filed Dec. 30, 2008, which applications are incorporated by reference herein.

TECHNICAL FIELD

The present invention relates to a unit for transferring products.

More exactly, the present invention finds application in automatic machines for manufacturing consumer items.

BACKGROUND ART

In particular, the unit is designed for use in production machines equipped with a first conveyor feeding a succession of components at a first speed and at a predetermined frequency through a first station, and a second conveyor feeding a continuous succession of items at a second speed different to the first, and at the same frequency, through a second station. The unit in question is designed to transfer components from the first station to the second, so that they can be paired with the succession of items advancing on the second conveyor.

The transfer unit comprises at least one transport head capable of movement cyclically between the first and second stations in such a way as to pick up at least one component during each cycle from the first conveyor, and place it in association with a relative item advancing on the second conveyor.

The transport head is set in motion by a drive system at a speed varying in the course of each cycle between the aforementioned first speed registering at the first station and the second speed registering at the second station.

A transfer unit of the type outlined above, while suitable as a means of pairing components with items of whatever nature, finds application to advantage in the nappy/diaper manufacturing industry for the purpose of transferring such items or their components, typically adhesive tabs or layers of absorbent material, onto flat nappy/diaper blanks. It is to this type of use that reference will be made explicitly in the following specification, albeit implying no limitation in scope.

In effect, it is the practice with machines for manufacturing nappies, or diapers, to prepare a continuous strip of flat nappy/diaper blanks, unfinished, and thereafter apply finishing components to the blanks, such as elasticated tabs on either side, or crotch inserts of absorbent material, etc. . . . .

Since the components and the nappies/diapers are normally of dissimilar length, the strip of blanks and the components are supplied at different speeds to the transfer unit. Consequently, to avoid damaging both the components and the strip, and to ensure the components are not positioned wrongly on the strip, the machine must include a transfer unit equipped with transport heads such as will take up the single components at the speed with which they are caused to advance, vary their own speed during the transfer movement, and finally deposit the components on the strip at the same speed as the selfsame strip.

This effect is produced by keying the transport heads to the driven shaft of a transmission system using non-circular gears, such as will allow of converting the rotation of a drive shaft, turning at constant speed, into rotary motion of which the speed is variable periodically according to a predetermined law of motion.

In effect, depending on the profile of the gears and the way in which they are paired positionally, variable transmission ratios and different laws of motion are obtainable.

In certain instances, alternatively, the transmission may utilize cam devices that will produce the same effect as eccentric gears, that is to say a variable speed of rotation at the driven shaft, while providing a purely mechanical control over the law of motion governing the operation of the transport heads.

As an electronic alternative to mechanical cam or non-circular gear type control media, an electronic cam can be used. In other words, the speed of rotation of the transport heads is determined by the speed of rotation of an electric motor driving the transfer unit directly.

Increasing or reducing the speed of rotation of the motor, the transport heads are caused to accelerate or decelerate correspondingly.

Notwithstanding the solutions aforementioned are effective and widely adopted, they present significant drawbacks deriving principally from a complex mechanical structure, which renders the unit particularly burdensome both from the purely constructional and dimensional standpoint, and in terms of cost.

The problem becomes particularly serious when switching to a different size or shape of product, given the need to change the speed of rotation, and therefore the law of motion governing the action of the transport head.

In addition, the demands of the market are such that manufacturers will seek constantly to improve the productivity of their equipment, and this means that a higher operating speed is required, which leads in turn to greater stresses on the structural mechanical parts of the machine. In particular, a faster speed of rotation at the transfer unit dictates a greater centrifugal force on the transport heads, higher acceleration, and increased wear on mechanical components.

In an attempt to overcome these drawbacks, transfer units with two or three transport heads have been proposed, as disclosed in reference EP0743843, by way of example.

Each head is associated with a cylindrical body aligned coaxially on a fixed axis. The cylindrical bodies are mutually concentric and rotatable one independently of another, each driven by a respective motor. Each head is therefore governed by a respective law of motion.

Disadvantageously, given the particular structure and dimensions of the mechanisms by which motion is induced in each transport head, these machines can operate only with a limited number of transport heads. In effect, a number of heads greater than three would create considerable difficulties in terms of dimensions, weights and structural complexity.

DISCLOSURE OF THE INVENTION

In the light of the foregoing, the primary object of the present invention is to provide a unit for transferring products, such as will be capable of overcoming the drawbacks mentioned above.

Within the scope of this primary object, a further object of the invention is to provide a transfer unit that will allow control over a plurality of transport heads, while keeping the overall dimensions of the unit suitably compact and ensuring that its structure remains uncomplicated.

Another object of the invention is to set forth a transfer unit that can be adapted easily and as required to changes in product size and different speeds of rotation, without the single component parts of the unit, and particularly the transport heads, being subjected to excessive stresses and wear.

The stated objects are substantially realized in a unit for transferring products according to the present invention, as recited in the appended claims.

BRIEF DESCRIPTION OF THE DRAWINGS

The invention will now be described in detail, by way of example, with the aid of the accompanying drawings, in which.

DETAILED DESCRIPTION OF THE PREFERRED EMBODIMENTS OF THE INVENTION

Figure 1:
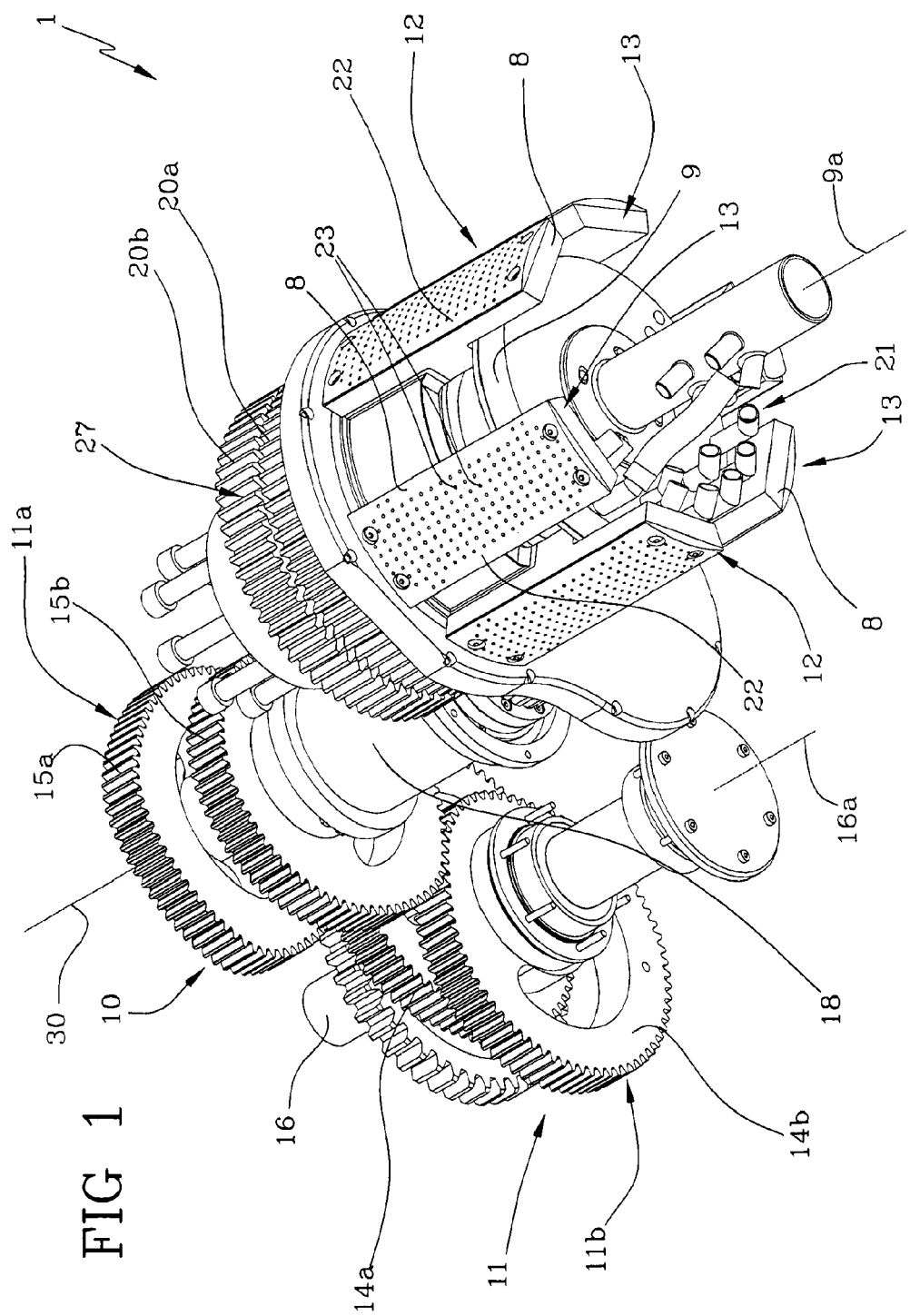
FIG. 1 shows a preferred embodiment of a unit for transferring products, viewed in perspective from the front.

In FIG. 1, numeral 1 denotes a unit for transferring products, in its entirety, designed for application to a machine for manufacturing consumer items.

In particular, the unit 1 for transferring products is designed advantageously for use in a machine manufacturing nappies, or diapers.

Figure 4:
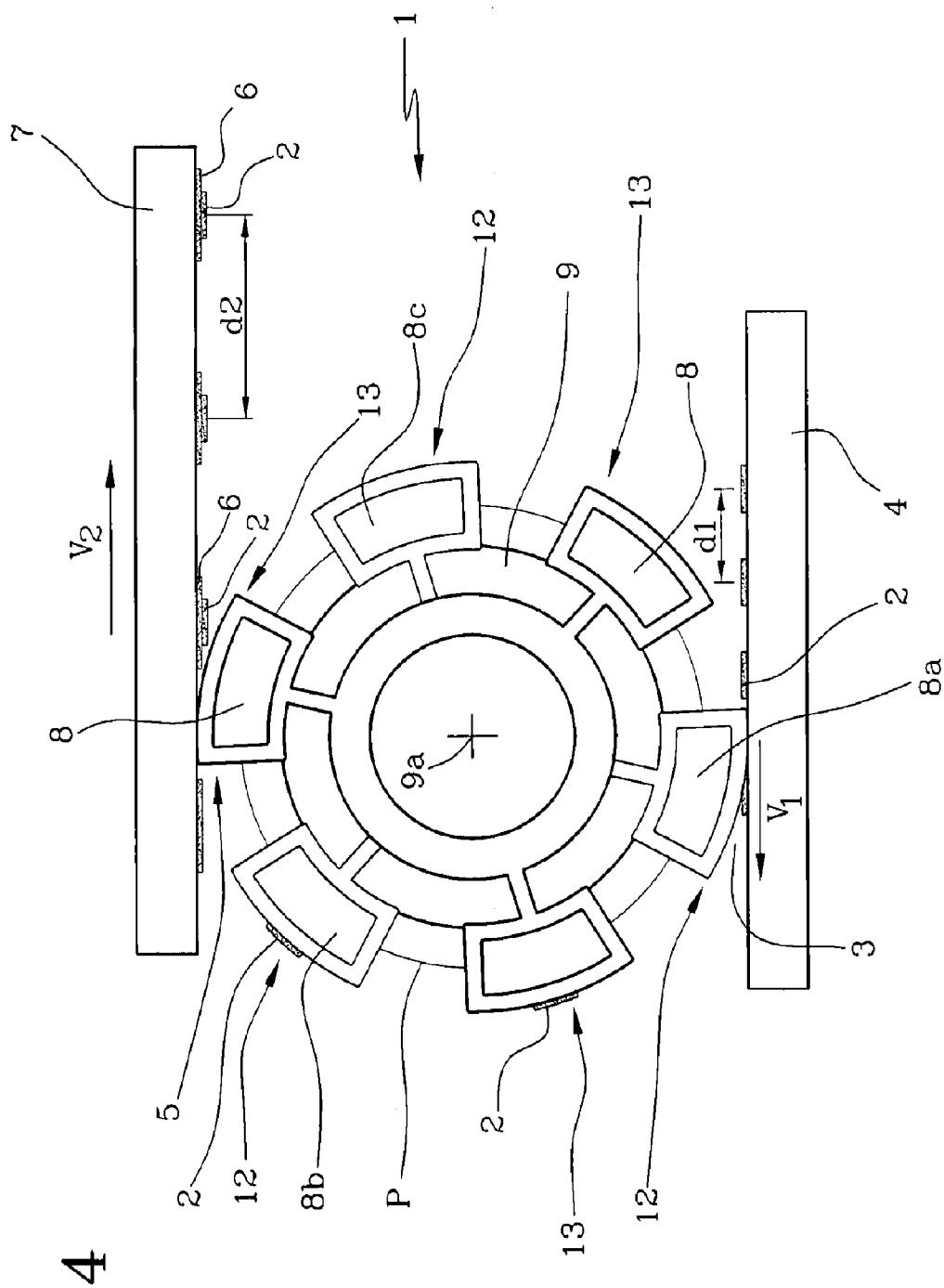
FIG. 4 is a schematic view showing the transfer unit according to the present invention, positioned between two conveyors.

As illustrated in FIG. 4, the unit in question is designed to take up nappy/diaper components 2 singly and in succession at a pick-up station 3, to which the components 2 are fed on a first conveyor 4 at a given linear velocity v1 and at a predetermined frequency, and to place the selfsame components 2 on respective items 6 at a delivery station 5, for example on a strip consisting in a continuous succession of flat nappy/diaper blanks, caused to advance on a second conveyor 7 at a linear velocity v2 different to v1 and at the same frequency as that with which the components 2 are fed to the pick-up station 3.

Given that the items 6 advancing on the second conveyor 7 are generally of dissimilar proportions to the components 2 advancing on first conveyor 4, and therefore spaced apart at a different distance between centres, for example greater than the distance between centres of two successive components 2, the distance between two successive components 2 taken up at the pick-up station 3 must be altered before the components 2 are placed on the items 6.

Accordingly, the unit 1 in question for transferring products is a device capable of varying the distance between successive components 2 taken up in succession at a distance denoted d1 from the first conveyor 4 at the pick-up station 3, before placing them on the second conveyor 7 at the delivery station 5, in the same sequence, at a distance denoted d2 greater or less than distance d1.

The unit 1 comprises a plurality of revolving transport heads 8 arranged on a drum 9 positioned between the pick-up station 3 and the delivery station 5, which are capable of movement around a circular path P centred on the axis 9a of the drum 9. The transport heads 8 advance in succession through the pick-up station 3 and the delivery station 5. As illustrated schematically in FIG. 4, the axis 9a about which the drum 9 rotates is orthogonal to the direction followed by at least one of the conveyors. The transport heads 8 are embodied preferably as aspirating plates, each presenting a surface 22 with a plurality of holes 23.

Each transport head 8 is connected to a pneumatic system 21 such as will create a partial vacuum on the surface 22 of the relative aspirating plate.

The transfer unit 1 further comprises a drive system 10 comprising a plurality of units 11 by which motion is induced in the transport heads 8.

In the preferred embodiment described and illustrated, the drive system comprises two such motion-inducing assemblies, denoted 11a and 11b.

The transport heads 8 are organized so as to form at least a first group 12 and a second group 13, each set in motion by a respective first assembly 11a and a respective second assembly 11b.

Each group 12 or 13 of heads will comprise preferably a set of at least three transport heads 8, governed by a single law of motion. The transport heads 8 of each group 12 and 13 are interconnected in such a way as to follow the one law of motion.

As illustrated schematically in FIG. 4, the transport heads 8 of a single group 12 or 13 are associated with a respective body 28 or 29, rotatable about the axis 9a of the drum 9.

The first group 12 of transport heads is uncoupled from and movable independently of the second group 13, each group being governed by a respective law of motion.

To advantage, the transport heads 8 are arranged around the drum 9 in such a way that the heads 8 of the first group 12 are alternated with the heads 8 of the second group 13.

Each motion-inducing assembly 11a and 11b comprises at least one first gear 14a and 14b and at least one second gear 15a and 15b, engaged in meshing contact one with another and combining to set the associated group of transport heads in motion. In particular, the first gears 14a and 14b of the two motion-inducing assemblies are driving members keyed directly to a drive shaft 16 set in rotation by a motor 24.

Accordingly, each driving member 14a and 14b meshes with the respective second gear 15a and 15b, or driven member, by which motion is relayed through the agency of suitable transmission means 27, described hereinafter, to the respective group 12 and 13 of transport heads.

Each first and second gear, driving and driven member alike, presents a particular profile of non-circular geometry: consequently, the pairing between a first gear 14a or 14b and a second gear 15a or 15b, and the motion transmitted one to another, establishes a particular law of motion that is transmitted in turn to the associated set of three transport heads 8. In other words, the movement of each group 12 and 13 of heads will conform to a particular law of motion, established by the geometry of the non-circular gears and by the timing between the gear pairs, such as will cause the transport heads 8 to alternate between acceleration and deceleration.

The profiles of the gears can be identical one with another or, preferably, dissimilar one to another.

To reiterate, the law of motion is determined in part by the timing of the gears, that is to say the mutual angular positions of the driving and driven members.

In detail, the first non-circular gears 14a and 14b or driving members of both motion-inducing assemblies 11a and 11b are keyed to a common drive shaft 16 constituting the main power transmission component of the drive system 10.

The two first gears 14a and 14b are set in rotation as one on the shaft 16, which is driven by the single motor 24 aforementioned.

The transfer unit 1 further comprises a control unit 25, serving to monitor and govern the operation of the motor 24 driving the main shaft 16.

Also forming part of the unit 1 is a driven shaft 17 extending parallel to the main drive shaft 16. The second gears 15a and 15b of the two motion-inducing assemblies 11a and 11b are mounted coaxially to the driven shaft 17. One only of the two second gears, in particular the second gear 15a of the first motion-inducing assembly 11a, is keyed directly to the driven shaft 17 at a point near to one end 17a, and serves thus to set this same shaft in rotation. Conversely, the other second gear 15b, forming part of the second motion-inducing assembly 11b, is associated with a first end 18a of a sleeve denoted 18. The sleeve 18 is mounted concentrically to the driven shaft 17 and rotatable independently of this same shaft. In effect, the driven shaft 17 and the sleeve 18 are interfaced advantageously by way of bearings 26, preferably ball bearings, which allow the shaft 17 and the sleeve 18 freedom of rotation one relative to the other.

Set in rotation by the main drive shaft 16, the first gears 14a and 14b mesh with the second gears 15a and 15b, so that these likewise are set in rotation; rotary motion is then transmitted by the second gears 15a and 15b to the driven shaft 17 and the sleeve 18.

The driven shaft 17 and the sleeve 18 are configured in such a way as to drive the first group 12 and the second group 13 of transport heads, respectively, by way of the aforementioned transmission means 27.

In the preferred configuration described and illustrated, at least two sets of transmission means 27 are used, each connecting a motion-inducing assembly 11a and 11b with the respective group 12 and 13 of transport heads and thus causing the heads to follow the respective law of motion.

Figure 2:
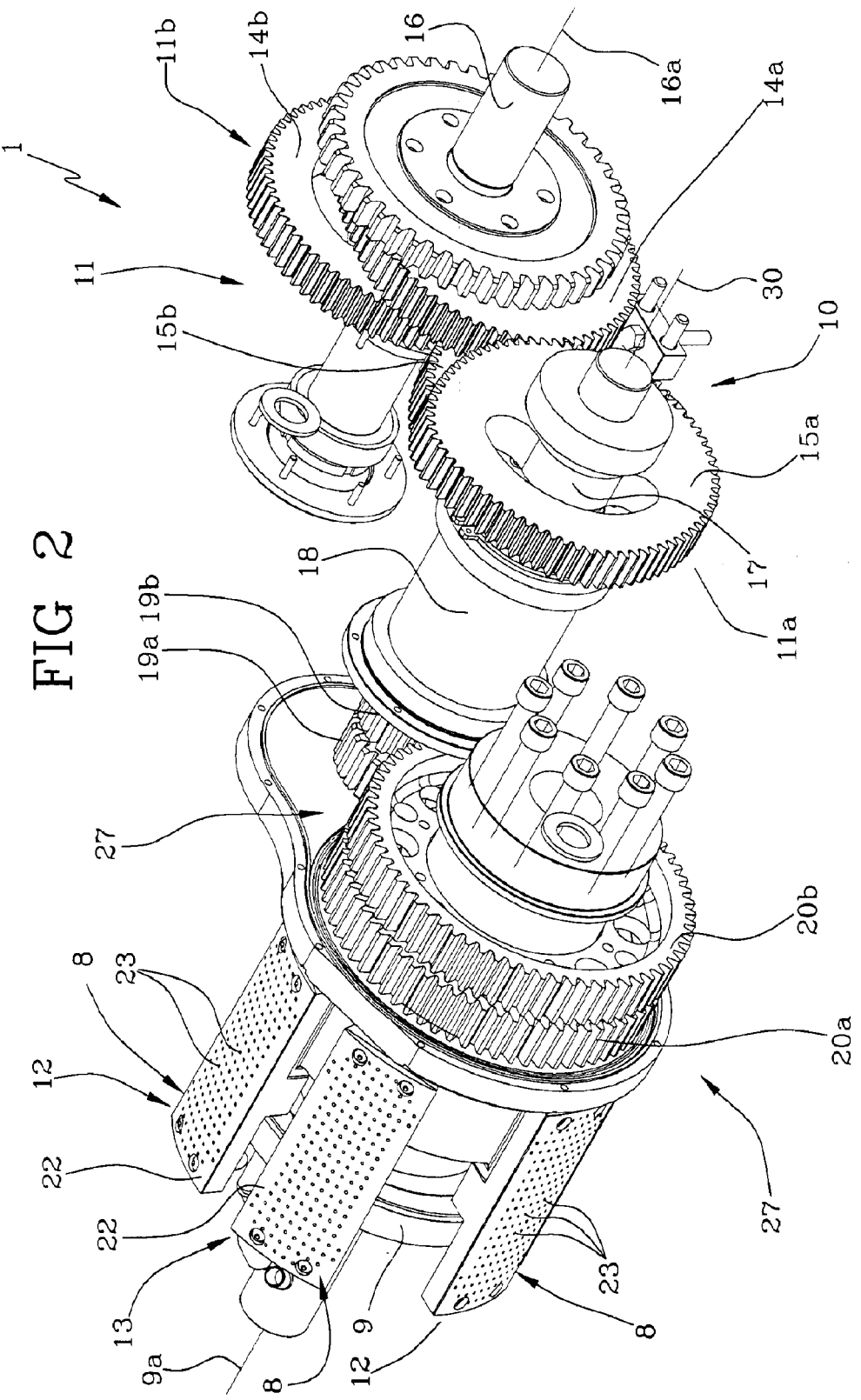
FIG. 2 shows the unit of FIG. 1, viewed in perspective from the rear.
Figure 3:
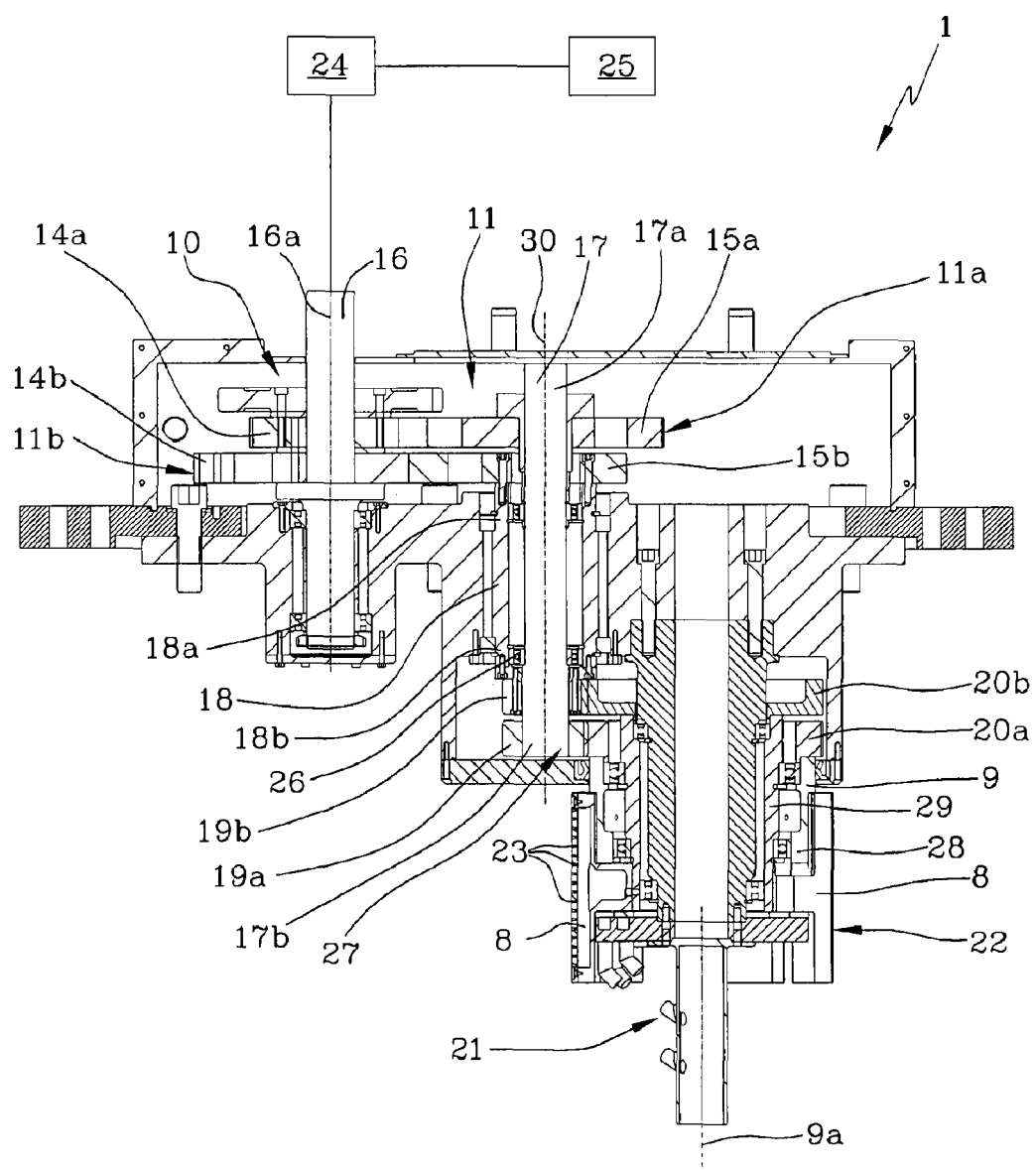
FIG. 3 is a plan view of the unit for transferring products according to the present invention, illustrated in section.

As discernible in FIG. 2 and in the sectional illustration of FIG. 3, the transmission means 27 each comprise a first circular gear 19a and 19b and a second circular gear 20a and 20b meshing one with another, by which the law of motion is transmitted to the respective group 12 and 13 of heads.

The first circular gears 19a and 19b of the transmission means 27 are mounted coaxially on the driven shaft 17, one keyed to a second end 17b of the selfsame shaft 17 and the other keyed to a second end 18b of the sleeve 18.

The second circular gears 20a and 20b are concentric with the axis 9a of the drum 9 around which the transport heads 8 are arranged.

The second gears 20a and 20b in their turn are rigidly associated with cylindrical sleeves 28 and 29, rotatable about the axis 9a of the drum 9. The groups 12 and 13 of heads are mounted directly to these same sleeves.

The axis 9a of the drum 9 lies parallel both to the axis 30 of the driven shaft 17 and to the axis 16a of the main drive shaft 16.

Given that the gears 19a, 19b, 20a and 20b of the transmission means 27 serve simply to transmit the law of motion already established by the motion-inducing assemblies 11a and 11b, their profile is symmetrical and circular.

By contrast, the gears 14a, 14b, 15a and 15b of the two motion-inducing assemblies 11a and 11b are characterized by an asymmetrical and non-circular geometry, as these gears must function as cam profiles able to vary the angular velocity of moving parts connected to them.

Depending on the particular geometry of the profile presented by each gear 14a, 14b, 15a and 15b and on the angular timing selected for the corresponding pairs, each group 12 and 13 of heads will be governed by a respective law of motion, alternating periods of acceleration with periods of deceleration; in this way, the components 2 taken up from the first conveyor 4 can be placed on the second conveyor 7 at a distance d2 different to the distance d1 at which the selfsame components 2 are spaced on the first conveyor 4.

The drive system 10 is designed to operate the groups 12 and 13 of heads in such a way that each transport head 8 of each group 12 and 13 passes through the pick-up station 3 at a first velocity v1 and through the delivery station 5 at a second velocity v2.

Thus, the velocity of the heads 8 will vary cyclically during the rotation of the drum about its axis 9a. More exactly, each head 8 moves at a constant velocity v1 during its passage through the pick-up station 3, then accelerates and decelerates alternately in passing from the pick-up 3 station to the delivery station 5 and transitioning to velocity v2, which is maintained constant during its passage through the delivery station 5; thereafter, the head accelerates and decelerates in alternation once again between the delivery station 5 and the pick-up station 3, finally returning to velocity v1 at a point upstream of the pick-up station 3.

The alternation between acceleration and deceleration during the passage from the pick-up station 3 to the delivery station 5, and between deceleration and acceleration during the passage from the delivery station 5 to the pick-up station 3, is explained by the presence of multiple transport heads 8 making up each group 12 and 13 and governed by the same law of motion.

In the example of FIG. 4, the transfer unit takes up a component 2 from the pick-up station 3 and transports it to the delivery station 5, rotating clockwise as viewed in the drawing.

As a first transport head 8a of the first group 12 passes through the pick-up station 3 at velocity v1, a transport head 8 of the second group 13 will be passing through the delivery station 5, followed closely by a second head 8b of the first group 12, which must therefore accelerate from velocity v1 to v2, and preceded by a third head 8c of the first group 12, which must decelerate from velocity v2 to v1. Accordingly, given that the three heads 8a-8b-8c are rigidly associated one with another, their movement along the path P within the sectors extending from the pick-up station 3 to the delivery station 5, and from the delivery station 5 to the pick-up station 3, will include periods of acceleration alternated with periods of deceleration.

Still referring to FIG. 4, the transport heads 8 of each group 12 and 13 are arranged around the drum 9, preferably equispaced at 120°, and set in motion clockwise as viewed in the drawing, so that when a first head 8a, say, of the first group 12, is positioned at the pick-up station 3 to take up a component 2 from the first conveyor 4, a second head 8b of the same group is positioned a short distance upstream of the delivery station 5 in readiness to place a component 2 on a relative item 6 carried by the second conveyor 7, whilst a third head 8c of the same first group 12 is positioned a short distance beyond the delivery station 5, having just released a component 2 to a item 6 advancing on the second conveyor 7.

The transport heads of the second group 13 are phased differently to the heads of the first group 12, in such a way that when the heads of the first group advance at velocity v1, allowing one head to take up a component 2 from the pick-up station 3, a head 8 of the second group will be advancing at velocity v2 in order to release a component 2 at the delivery station 5.

Accordingly, the moment immediately after a component 2 has been picked up, the first group 12 will accelerate and then decelerate, whilst the second group 13 will decelerate and then accelerate.

As a result of the two groups 12 and 13 being mutually out of phase, the distance between two successive heads on the drum will reduce and increase alternately between a minimum and a maximum, thereby changing the distance between successive components from d1, when picked up from the first conveyor, to d2 when released to the second conveyor.

The change in angular velocity whereby the single transport heads are able to alternate during each cycle between v1 and v2, is induced in the selfsame heads by the drive system 10, and in particular by the asymmetric profiles of the non-circular gears 14a, 14b, 15a and 15b. In other words, the profile of each gear is irregular, with certain portions projecting radially farther than others.

The drawbacks associated with the prior art are overcome by the present invention and the stated objects duly realized, with important advantages.

First and foremost, it will be seen that by adopting a plurality of transport heads grouped in sets of three, it becomes possible to increase productivity without putting the single heads under excessive strain. With a greater number of transport heads, in effect, the frequency with which the transfer unit cycles through the pick-up and delivery stations can be raised, and without any inordinate increase in the rotational speed of the drum carrying the heads. This means that the transport heads are subjected neither to excessive centrifugal forces, nor to high accelerations.

With this type of configuration, the transfer unit is readily adaptable to different product sizes, given that the frequency with which components are picked up and released can be varied without difficulty.

Moreover, by grouping the transport heads in sets, the number of heads can be increased without complicating and weighing down the structure of the transfer unit. In the preferred configuration described and illustrated, in effect, six transport heads can be operated, applying only two different laws of motion. Consequently, it would be possible for example to increase the number of heads to eight with just the two laws of motion, or to nine with three laws of motion. Other configurations are possible, at all events, likewise grouping together a given number of transport heads governed by a single law of motion.

Each law of motion is determined both by mechanical means, through the timing and geometry of the non-circular gear pairs, and by electronic means, through the operation of the control unit governing the motor to which the drive shaft is coupled.

Accordingly, the cyclical speed of rotation can be varied without the need for costly and complicated replacement procedures involving the mechanical part of the transmission.

According to the present invention, furthermore, several transport heads can be operated using a single motor, thereby simplifying the structure significantly, as well as reducing the bulk and weight of the unit as a whole.

Finally, it will be appreciated that the foregoing description of the transfer unit 1 in a machine 2 for manufacturing nappies/diapers remains valid similarly for a transfer unit used in any other kind of production machine to pick up components of whatever description, advancing at a given velocity v1, and pair them with respective items of whatever description advancing at a velocity v2 greater or less than v1.

The invention claimed is:

1. A unit for transferring products, comprising:
a plurality of transport heads by which products are transferred, and a drive system comprising a plurality of assemblies by which motion is induced in the transport heads, the plurality of transport heads comprising a first group of heads and a second group of heads, driven respectively by a first motion-inducing assembly and a second motion-inducing assembly;
each motion-inducing assembly comprising at least one first gear and at least one second gear, each having a non-circular profile;
the first non-circular gears of the first motion-inducing assembly and the second motion-inducing assembly being keyed onto a single main drive shaft by which the drive system is activated and kept in motion.

2. A unit as in claim 1, wherein the first group of heads and the second group of heads each comprise a set of at least three transport heads.

3. A unit as in claim 1, wherein the transport heads are movable along a circular path centered on a single fixed axis.

4. A unit as in claim 1, wherein the transport heads revolve around a drum and are arranged in such a way that the heads of the first group will be alternated with the heads of the second group.

5. A unit as in claim 1, wherein the transport heads each comprise an aspirating plate having a surface furnished with a plurality of holes, and are each connected to a pneumatic system to create a partial vacuum on the surface of the relative plate.

6. A unit as in claim 1, wherein the first non-circular gear and the second non-circular gear are paired one with another and combine to impose a suitable law of motion on the respective group of heads, determined by a geometry of the respective non-circular profiles.

7. A unit as in claim 1, wherein the drive system is set in motion by a single motor.

8. A unit as in claim 7, wherein the single motor sets the single drive shaft in motion.

9. A unit as in claim 1, wherein the second non-circular gears of the first motion-inducing assembly and the second motion-inducing assembly are mutually coaxial and associated respectively with a driven shaft and with a sleeve.

10. A unit as in claim 9, wherein the second non-circular gear of the first motion-inducing assembly is keyed to the driven shaft in such a way as to set the driven shaft in rotation, and the second non-circular gear of the second motion-inducing assembly is associated with the sleeve coupled concentrically with the driven shaft, in such a way that the sleeve and the shaft can be set in rotation governed by different laws of motion.

11. A unit as in claim 9, wherein the driven shaft and the sleeve are aligned concentrically on a single axis and rotatable independently one of another, thereby allowing the two second non-circular gears to rotate likewise independently of one another.

12. A unit as in claim 1, wherein the first non-circular gears and the second non-circular gears each have an irregular profile, such that the interaction of the first gear and the second gear forming part of the same motion-inducing assembly produces alternating periods of acceleration and deceleration in the movement of the respective group of transport heads.

13. A unit as in claim 1, wherein the first group of transport heads and the second group of transport heads are driven respectively by the first motion-inducing assembly and the second motion-inducing assembly via a respective transmission mechanism.

14. A unit as in claim 12, wherein each transmission mechanism comprises at least two symmetrical circular gears.

15. A unit for transferring products, comprising:
a plurality of transport heads by which products are transferred, and a drive system comprising a plurality of assemblies by which motion is induced in the transport heads, the plurality of transport heads comprising a first group of heads and a second group of heads, driven respectively by a first motion-inducing assembly and a second motion-inducing assembly;

each motion-inducing assembly comprising at least one first gear and at least one second gear, each having a non-circular profile;

wherein the second non-circular gears of the first motion-inducing assembly and the second motion-inducing assembly are mutually coaxial and associated respectively with a driven shaft and with a sleeve.

16. A unit as in claim 15, wherein the second non-circular gear of the first motion-inducing assembly is keyed to the driven shaft in such a way as to set the driven shaft in rotation, and the second non-circular gear of the second motion-inducing assembly is associated with the sleeve coupled concentrically with the driven shaft, in such a way that the sleeve and the shaft can be set in rotation governed by different laws of motion.

17. A unit as in claim 15, wherein the driven shaft and the sleeve are aligned concentrically on a single axis and rotatable independently one of another, thereby allowing the two second non-circular gears to rotate likewise independently of one another.

* * * * *